United States Patent [19]

Rigopulos et al.

[11] 4,143,203
[45] Mar. 6, 1979

[54] PARTICULATE SUPPORT MATERIAL

[75] Inventors: Peter N. Rigopulos, Boxford; Charles W. Desaulniers, Franklin; David E. Doucette, Wakefield, all of Mass.

[73] Assignee: Amicon Corporation, Lexington, Mass.

[21] Appl. No.: 668,425

[22] Filed: Mar. 19, 1976

[51] Int. Cl.$^2$ .......................... B32B 5/16; B32B 9/04
[52] U.S. Cl. .................................. 428/407; 428/403; 526/23; 526/49; 528/502
[58] Field of Search ................. 428/403, 402, 407; 106/137, 193 R; 526/23, 26, 41, 50, 51, 49; 528/502

[56] References Cited

U.S. PATENT DOCUMENTS

| 2,548,853 | 10/1948 | Baker | 526/23 X |
|---|---|---|---|
| 2,719,144 | 9/1955 | Shearer et al. | 526/51 X |
| 2,861,059 | 11/1958 | Mowry et al. | 526/23 X |
| 3,758,449 | 9/1973 | Hoppe et al. | 526/23 X |
| 3,948,870 | 4/1976 | Stoy et al. | 526/41 X |

*Primary Examiner*—George F. Lesmes
*Assistant Examiner*—R. Eugene Varndell, Jr.

[57] ABSTRACT

Particles having a mean diameter from 0.1 to 50 micrometers and having a solid core of water-impermeable polyacrylonitrile and a partially hydrolyzed hydrophilic surface layer enclosing the core containing from 0.001 to 0.8 milliequivalents of carboxyl or carboxylate groups per dry gram, the surface layer amounting to 0.01 to 20% by weight of the particles, are useful as a solid phase insoluble support to which biospecific reagents such as antigens or antibodies can be coupled. Variants include supports in which N-hydroxysuccinimide or various spacer arms are coupled to the carboxyl or carboxylate groups.

4 Claims, No Drawings

PARTICULATE SUPPORT MATERIAL

This invention relates to a particulate solid support material for use in making a biospecific adsorption medium for solid phase immunoassay, immunoadsorption, or other affinity separation or molecular diffusion processes.

The particulate material of the present invention is in the form of particles having a mean diameter from 0.1 to 50 micrometers and having a solid core of water-impermeable polyacrylonitrile and a hydrophilic surface layer enclosing the core consisting essentially of partially hydrolyzed polyacrylonitrile having covalently bonded carboxyl or carboxylate groups in an amount from 0.001 to 0.8 milliequivalents per dry gram of particles the surface layer amounting to 0.01 to 20% by weight of the particles. The particles are irregular in shape, although they are generally approximately spherical. The hydrophilic surface layer may have a thickness from 10 to 2,000 Angstrom units. In other embodiments of the invention, at least 10% of the carboxyl or carboxylate groups in the surface layer are covalently bonded to N-hydroxysuccinimide or to various conventional spacer arms such as polyaklylene glycols, polyvinyl alcohol, mono-, di-, and poly-saccharides, sugar alcohols, alkylene diamines, amino acids, and acyl dihydrazides.

The particulate material of the present invention is characterized by being in the form of opaque, visible, hard dense solid particles of high molecular weight polymer which are relatively rigid and incompressible and which have a specific gravity greater than 1, up to 1.2, so that they can readily be separated from water and organic solvents by microporous filters, by centrifugation, or even by simple settling under the influence of gravity. The particles can readily be pipetted and can be pelleted by centrifugation. They are resistant to cracking and breaking when subjected to centrifugation at accelerations up to 10,000 g and they exhibit little or no non-specific absorption; the surface layer is hydrophilic and capable of being hydrated through hydrogen bond interactions with water while the core remains hydrophobic; it contains in addition to carboxyl or carboxylate groups, both amide and imide groups covalently bonded to the polyacrylonitrile of the core. Even more important is the fact that the particles of the present invention, unlike many of the solid supports of the prior art, exhibit, when used in column chromatography, little or no tendency to cause separation of materials on the basis of molecular weight in the range from 500 upwards, to 5,000,000 or more in molecular weight. It is believed that this characteristic results from the lack of any microreticulation or porosity in the core of the particles which would permit competitive diffusion of molecules in the aforesaid molecular weight range to and from the interior of the particles.

The particles made in accordance with the present invention may have a mean particle size within the range 0.1 to 50 micrometers, as set forth above; however, the range of distribution of particle diameters about the mean value is preferably within 20%, i.e., ±20%, of the mean diameter in any given case for best results. When the support particles are intended for use in agglutination assays, the mean particle size is generally from 0.1 to 20 micrometers, while for immunoassay it is preferably from 1 to 5 micrometers, and for preparative column procedures it is preferably from 40 to 50 micrometers.

The density or specific gravity of the particles should be greater than 1 in order to permit separation from water by settling; preferably it is from 1.1 to 1.2.

The carboxyl groups can be present in the form of free carboxyl groups or in their equivalent form of salts of organic or inorganic bases including ammonium hydroxide, preferably alkali metal salts such as sodium or potassium, which can, if desired, be readily converted to free carboxyl groups by acidification in an aqueous medium. The proportion of total carboxyl and carboxylate groups may vary from 0.001 to 0.8 milliequivalents per dry gram of solid particles depending on specific applicational requirements.

The particulate support material of the present invention can be made from polyacrylontrile, including copolymers of acrylonitrile with minor amounts, up to 10% by weight, of comonomers such as methyl acrylate or ethyl acrylate (sold under the trade name Orlon).

In making the material of the present invention, the polyacrylonitrile, which is available in the form of relatively large beads or powder having a specific gravity of approximately 1.2, is first reduced in size by grinding, by passing through a Waring Blendor, or by subjecting a slurry of the particles in water or other inert liquid to an ultrasonic vibrator, or by any other suitable procedure to produce a mass of particles within the desired range of particle diameters. The particles are then subjected to partial hydrolysis by heating in an aqueous solution of acid such as sulfuric acid at a temperature of the order of 75° to 95° C. until the surface layer only of the particles, amounting to 0.01 to 20% by weight of the particles and having a thickness of 10 to 2000 Angstrom units, has been hydrolyzed to produce carboxyl groups in the desired amount. In the course of the hydrolysis reaction, there are formed in addition to the carboxyl groups both amide and imide groups. The particles are then separated from the acid, neutralized, and washed with water. While acid hydrolysis is preferred, partial hydrolysis can also be carried out in aqueous alkaline media. The product can be used in the form of a slurry in water containing up to 30% solids by weight, or if desired, can be dried for shipping and storage before use. The product is in the form of rigid, nodular, non-porous particles with the carboxyl or carboxylate group reaction sites freely accessible to bulk solvent, providing maximal exposure of ligands when coupled to the carboxyl groups. The particles combine the stability of the highly insoluble hydrophobic water-impermeable polyacrylonitrile core with the desirable properties of a hydrogel in the surface layer. The fact that the activity, either in the form of carboxyl or carboxylate groups or in the form of ligands covalently coupled to the carboxyl groups, is confined to the surface layer, in contrast to many of the particulate supports of the prior art, favors desorption and equilibration under mild conditions with minimal denaturing because of the kinetic accessibility of the ligand to solvent changes.

The product thus formed having a surface layer containing carboxyl or carboxylate groups can be modified by esterifying at least 10%, preferably at least 30% of the carboxyl and carboxylate groups to form N-hydroxysuccinimide ester groups. This esterification can be carried out by preparing a water-free suspension of the partially hydrolyzed polyacrylonitrile particles in an inert organic solvent such as dioxane, and mixing with the suspension N-hydroxysuccinimide and diisopropylcarbodiimide. This product likewise has a solid rigid water-impermeable core of polyacrylonitrile to which the N-hydroxysuccinimide ester groups as well as residual carboxyl or carboxylate groups are covalently bonded.

The product containing free carboxyl or carboxylate groups and no ester groups in the surface layer can be coupled with any of the usual ligands using any of the conventional coupling agents and spacer arms.

The product containing N-hydroxysuccinimide ester groups in the surface layer possesses the advantage that it can be coupled to any conventional ligand such as a protein without the necessity for using any separate coupling agent simply by mixing the product with a solution of the desired ligand in a suitable buffer such as aqueous sodium phosphate at pH 7-9. This coupling is preferably carried out at low temperature of the order of 0° to 10° C. with the particulate material preferably present in an amount from 0.1 to 1% by weight of the total solution. In coupling protein ligands to the product containing N-hydroxysuccinimide ester groups, the coupling reaction, in which the protein or amino acid displaces the N-hydroxysuccinimide, is preferably completed as rapidly as possible, within 16 hours or less, at a temperature below 20° C. in order to minimize hydrolysis of the N-hydroxysuccinimide ester groups. After coupling, any excess ligand together with displaced N-hydroxysuccinimide can be removed with the buffer solution by decantation or filtration, and any unreacted N-hydroxysuccinimide ester groups on the particles can be removed by mixing the particles with 0.01 molar aqueous monoethanolamine.

The product containing carboxyl or carboxylate groups in the surface layer can also be modified by bonding covalently to at least 10%, preferably at least 30% of the groups a layer no more than 20% by weight of parent carboxyl or carboxylate particle of a variety of conventional spacer arms by forming esters or amides with various difunctional compounds including polyalkylene glycols such as polyethylene glycols and polypropylene glycols, preferably those having low molecular weights from 62 to 550, polyvinyl alcohol, monosaccharides such as fructose, glucose, mannose, ribose, galactose, disaccharides such as sucrose, maltose, lactose, cellobiose, polysaccharides such as agarose, dextran, inulin, pectin, chitin, starch, cellulose, diamines such as ethylene diamine, hexamethylene diamine, 1,3-diamino-2-propanol, amino acids such as glycine, beta-alanine, 6-aminohexanoic acid, acyldihydrazides such as succinic dihydrazide, adipic dihydrazide. The coupling arm may have any of the usual chain lengths, being made from difunctional compounds having chain lengths from one to 15 or more atoms between the two reactive functional groups. The difunctional compounds forming the spacer arms can be reacted with the carboxyl or carboxylate groups of the particles to form covalent bonds by any conventional procedures including the use of coupling agents such as carbodiimides. Those spacer arms which themselves terminate in carboxyl or carboxylate groups can also be esterified with N-hydroxysuccimide to facilitate subsequent coupling to ligands such as proteins without the necessity of using separate coupling agents.

The following specific examples are intended to illustrate more clearly the nature of the present invention without acting as a limitation upon its scope.

EXAMPLE 1

Polyacrylonitrile powder (E. I. DuPont) having an intrinsic viscosity of 1.95 was ground with mortar and pestle, then stirred into a mixture of 1 part by weight of acetone with 2 parts by weight of water to form a slurry containing 10% by weight of particles. The slurry was then subjected to ultrasonic vibrations using a conventional vibrator at approximately 65° C. until microscopic examination showed the polymer to have a particle size averaging 2 micrometers in diameter with the size distribution within 20% of the mean diameter. The particles were generally spherical in shape, although they displayed substantial irregularities. The slurry was then subjected to ultrafiltration through a microporous membrane to remove the acetone while simultaneously diluting it with water, after which the slurry was concentrated by ultrafiltration and centrifugation to approximately 10% total solids.

With 2.0 kg. of slurry (10% total solids), there was mixed 1.6 kg. of 50% aqueous sulfuric acid at a temperature of 90° C. An additional 1.2 kg. of 98% sulfuric acid was mixed in slowly over a period of about 15 minutes and the mix was allowed to stand with sitrring at 90° C. for 30 hours until the desired extent of hydrolysis had been achieved. The slurry was then dumped into 11 liters of distilled water and allowed to settle overnight at room temperature. The supernatant liquid was removed by decantation, and the settled solid particles were washed repeatedly by decantation with fresh distilled water, approximately 2 hours being required for settling after each washing.

The washed slurry was then neutralized by stirring into it 25% by weight agueous sodium hydroxide solution until the pH of the slurry was 6-7. The neutralized slurry was then washed repeatedly by decantation with distilled water to remove the sodium sulfate and to provide a finished product in the form of a water slurry containing 5-10% by weight of solid particles ranging in diameter from 1 to 3 micrometers. The particles consisted of a core of water-impermeable hydrophobic polyacrylonitrile and a surface layer enveloping the core consisting of partially hydrolyzed polyacrylonitrile containing carboxyl, sodium carboxylate, amide, and imide groups covalently bonded to the polyacrylonitrile core, the number of carboxyl and carboxylate groups in the surface layer amounting to 0.34 milliequivalents per dry gram. The surface layer was hydrophilic but could readily be dried under vacuum at ambient (room) temperature and rehydrated by exposure to water.

The particles had a specific gravity of approximately 1.2 and could be subjected to centrifugation at 1750 g without substantial crushing or breaking of the particles.

The particles could readily be coupled with any of the usual spacer arms and/or ligands such as proteins or amino acids by any of the usual procedures, displaying a remarkably high capacity for coupling based on the weight of the particles.

EXAMPLE 2

A water slurry containing 20.6 grams of partially hydrolyzed polyacrylonitrile particles prepared as described in Example 1 was exchanged 5 times with anhydrous dioxane to provide 400 ml. of water-free suspension. To this suspension were added 4.742 gram of anhydrous N-hydroxysuccinimide and 5.20 gram of diisopropyl carbodiimide and the solution was stirred for 20 minutes at room temperature. The suspension was then centrifuged for 15 minutes at 1750 g during which time the particles were clumped together into a pellet from which the liquid was decanted. The pellet was then dispersed in water-free dioxane and again subjected to centrifugation and separation. The washing by decantation step was repeated, the amount of dioxane added in the final step being adjusted to provide a solids content of approximately 10% by weight. The amount of N-hydroxysuccinimide ester groups present was determined by the method of Schnaar and Lee, Biochemistry, Vol. 14, page 1536 (1975) to be 0.145 milliequivalents per gram dry weight of particles.

The product was found to be stable and free from swelling in anhydrous organic solvents such as ethanol, isopropanol, acetone, tetrahydrofuran and methyl ethyl ketone as well as in dioxane.

The product was readily coupled with protein ligands simply by mixing a water-free suspension of the particles (5% by by weight) in any of the foregoing solvents with a solution containing 10 milligrams of protein per millimeter in aqueous sodium phosphate buffer (0.01 molar). Higher strength buffers (e.g. 0.1 molar) are not preferred because of their tendency to cause aggregation of the particles, and amine buffers are preferably not used. The coupling is best carried out at 4° C. for 1 to 4 hours, or overnight, after which excess ligand in solution can be removed by filtration. Aqueous monoethanolamine (0.01 molar) can be used to quench any unreacted N-hydroxysuccinimide ester groups.

What is claimed is:

1. A particulate support material comprising particles having a mean diameter from 0.1 to 50 micrometers in which the range of particle sizes is within 20% of the mean diameter and the specific gravity of the particles is from 1.1 to 1.2, said particles having a core of water impermeable rigid polyacrylonitrile with a hydrophilic surface layer enclosing said core comprising hydrolyzed polyacrylonitrile having carboxyl or carboxylate groups in an amount from 0.2 to 0.5 milli-equivalent per dry gram of particles, said surface layer amounting to 0.01 to 20 percent by weight of said particles.

2. A particulate support material comprising particles having a mean diameter from 0.1 to 50 micrometers and having a core of water impermeable rigid polyacrylonitrile with a hydrophilic surface layer enclosing said core comprising hydrolyzed polyacrylonitrile having carboxyl or carboxylate groups in an amount of 0.001 to 0.8 milli-equivalent per dry gram of particles in which at least 10% of the total carboxyl and carboxylate groups are esterified to N-hydroxysuccinimide ester groups, said surface layer amounting to 0.01 to 20 percent by weight of said particles.

3. A particulate support material as claimed in claim 2 in which the range of particle sizes is within 20% of the mean diameter and the specific gravity of the particles is from 1.1 to 1.2 and in which at least 30% of the total carboxyl and carboxylate groups are esterified to N-hydroxysuccinimide ester groups.

4. A particulate support material as claimed in claim 2 in which at least 30% of the total carboxyl and carboxylate groups are esterified to N-hydroxysuccinimide groups and in which the total carboxyl and carboxylate groups amount to 0.2 to 0.5 milliequivalents per dry gram of particles.